(12) United States Patent
Nonnenmann et al.

(10) Patent No.: US 11,090,062 B2
(45) Date of Patent: Aug. 17, 2021

(54) MEDICAL SAWING TEMPLATE SYSTEM

(71) Applicant: Aesculap AG, Tuttlingen (DE)

(72) Inventors: Martin Nonnenmann, Wurmlingen (DE); Franz-Peter Firmbach, Emmingen-Liptingen (DE)

(73) Assignee: Aesculap AG, Tuttlingen (DE)

( * ) Notice: Subject to any disclaimer, the term of this patent is extended or adjusted under 35 U.S.C. 154(b) by 86 days.

(21) Appl. No.: 16/539,023

(22) Filed: Aug. 13, 2019

(65) Prior Publication Data

US 2019/0357920 A1 Nov. 28, 2019

Related U.S. Application Data

(63) Continuation of application No. PCT/EP2018/055533, filed on Mar. 7, 2018.

(30) Foreign Application Priority Data

Mar. 7, 2017 (DE) ...................... 10 2017 104 753.0

(51) Int. Cl.
| | |
|---|---|
| *A61B 17/58* | (2006.01) |
| *A61B 17/60* | (2006.01) |
| *A61F 2/00* | (2006.01) |
| *A61B 17/15* | (2006.01) |
| *A61B 90/00* | (2016.01) |

(52) U.S. Cl.
CPC .......... *A61B 17/154* (2013.01); *A61B 17/157* (2013.01); *A61B 2090/3916* (2016.02); *A61B 2090/3983* (2016.02); *A61B 2090/3991* (2016.02)

(58) Field of Classification Search
CPC combination set(s) only.
See application file for complete search history.

(56) References Cited

U.S. PATENT DOCUMENTS

| | | | |
|---|---|---|---|
| 6,712,824 | B2 | 3/2004 | Millard et al. |
| 7,377,924 | B2 | 5/2008 | Raistrick et al. |
| 7,520,880 | B2 | 4/2009 | Claypool et al. |
| 7,670,345 | B2 | 3/2010 | Plassky et al. |

(Continued)

FOREIGN PATENT DOCUMENTS

| | | |
|---|---|---|
| DE | 60216667 | 10/2007 |
| DE | 102015104223 | 9/2016 |

(Continued)

*Primary Examiner* — Sameh R Boles
(74) *Attorney, Agent, or Firm* — Lipsitz & McAllister, LLC

(57) ABSTRACT

The invention relates to a medical sawing template system, comprising an aligning apparatus for aligning a medical sawing template relative to a human or animal bone, which aligning apparatus comprises at least one fastening element receptacle for a fastening element fixable in bone, a first coupling member which is coupleable or coupled to a sawing template, a distance-changing device for varying a distance between the fastening element receptacle and the first coupling member, and an angle-changing device for varying an angle between the fastening element receptacle and the first coupling member, wherein the distance-changing device comprises a distance-setting member which is rotatable about a distance-setting member rotational axis, and/or wherein the angle-changing device comprises an angle-setting member which is rotatable about an angle-setting member rotational axis.

20 Claims, 7 Drawing Sheets

(56) References Cited

U.S. PATENT DOCUMENTS

Figure 1:
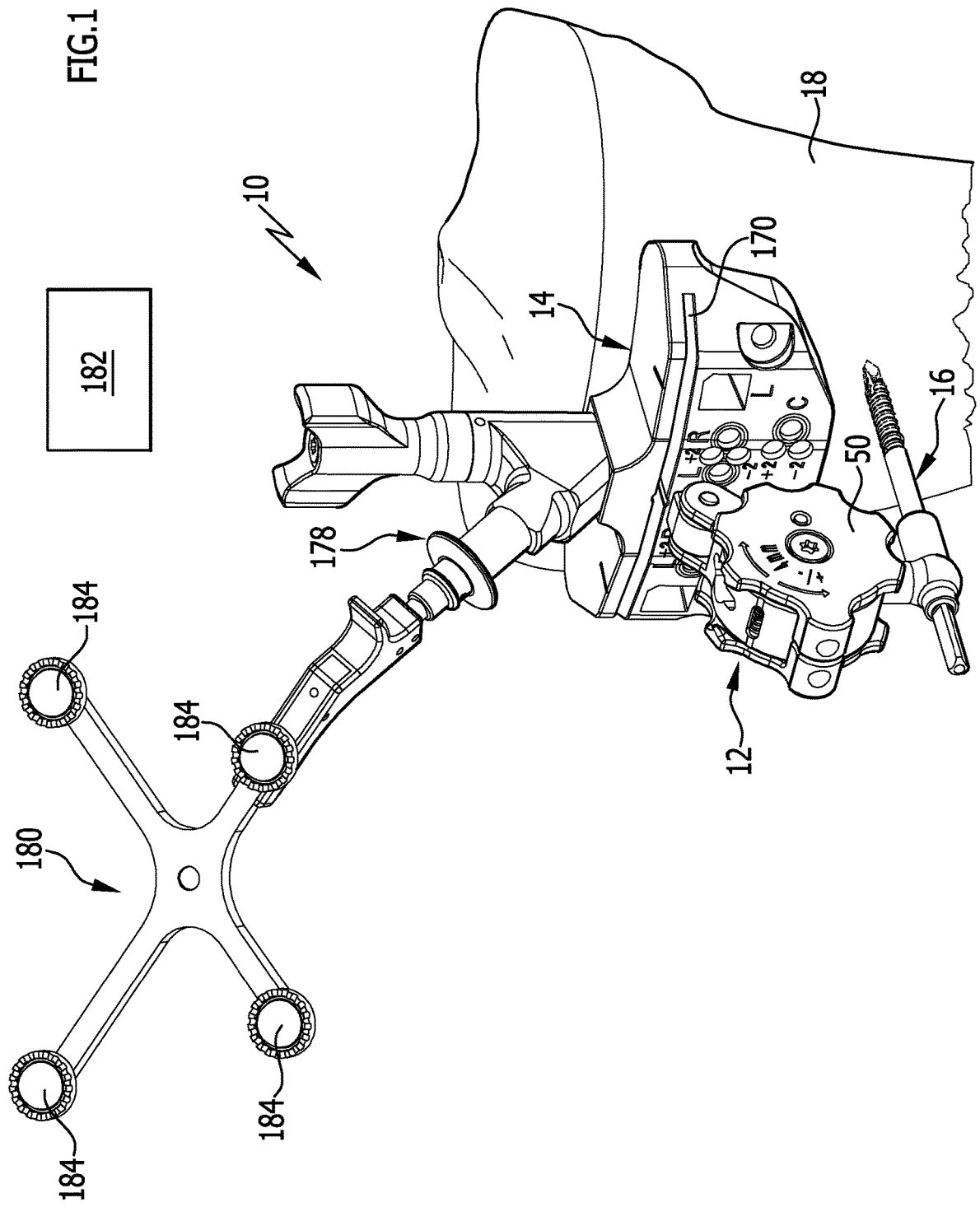

| | | |
|---|---|---|
| 7,744,600 B2 | 6/2010 | Rangaiah et al. |
| 7,909,831 B2 | 3/2011 | Axelson, Jr. et al. |
| 8,273,090 B2 | 9/2012 | Alvarez |
| 2002/0198531 A1 | 12/2002 | Millard et al. |
| 2006/0217733 A1 | 9/2006 | Plassky et al. |
| 2011/0060341 A1 | 3/2011 | Angibaud et al. |
| 2013/0158556 A1 | 6/2013 | Jones et al. |

FOREIGN PATENT DOCUMENTS

| | | |
|---|---|---|
| EP | 1269924 | 1/2003 |
| EP | 1444957 | 8/2004 |
| EP | 1690503 | 8/2006 |
| EP | 1691692 | 8/2006 |

MEDICAL SAWING TEMPLATE SYSTEM

CROSS-REFERENCE TO RELATED APPLICATIONS

This application is a continuation of international application number PCT/EP2018/055533 filed on Mar. 7, 2018 and claims the benefit of German application number 10 2017 104 753.0 filed on Mar. 7, 2017, which are incorporated herein by reference in their entirety and for all purposes.

FIELD OF THE INVENTION

The present invention relates to medical sawing template systems generally, and more specifically to a medical sawing template system, comprising an aligning apparatus for aligning a medical sawing template relative to a human or animal bone, which aligning apparatus comprises at least one fastening element receptacle for a fastening element fixable in bone, a first coupling member which is coupleable or coupled to a sawing template, a distance-changing device for varying a distance between the fastening element receptacle and the first coupling member, and an angle-changing device for varying an angle between the fastening element receptacle and the first coupling member.

BACKGROUND OF THE INVENTION

Medical sawing template systems of the kind described at the outset are used in particular in order to prepare bone faces before the implantation of joint endoprostheses. For example, template systems of that kind are used to partially resect a tibia and/or femur of a patient in order to prepare bone faces on which components of the joint endoprosthesis are fixed, for example by driving into the bone cavities, fixing with bone cement, and/or bone fastening means like, e.g., bone screws or bone nails.

In order to be able to align a sawing template, in particular a guide opening thereof for a saw blade, in the desired way in order to be able to ensure an optimal positioning of the joint components, a height and an inclination of the guide perforation of the sawing template may be set in a simple manner with the aligning apparatus. This is made possible, for one, by means of the distance-changing device with which, for example, the first coupling member may be translationally moved and, for another, by means of the angle-changing device with which an inclination of the first coupling member is settable with the sawing template.

Taking into account that very little space is available in the implantation of a knee joint endoprosthesis, it is desirable to configure the sawing template system as compactly as possible. In addition, the handling thereof should be simple and intuitive for a surgeon.

SUMMARY OF THE INVENTION

In a first aspect of the invention, a medical sawing template system comprises an aligning apparatus for aligning a medical sawing template relative to a human or animal bone. The aligning apparatus comprises at least one fastening element receptacle for a fastening element fixable in bone, a first coupling member which is coupleable or coupled to a sawing template, a distance-changing device for varying a distance between the fastening element receptacle and the first coupling member, and an angle-changing device for varying an angle between the fastening element receptacle and the first coupling member. The distance-changing device comprises a distance-setting member which is rotatable about a distance-setting member rotational axis, and/or the angle-changing device comprises an angle-setting member which is rotatable about an angle-setting member rotational axis.

BRIEF DESCRIPTION OF THE DRAWING FIGURES

Figure 2:
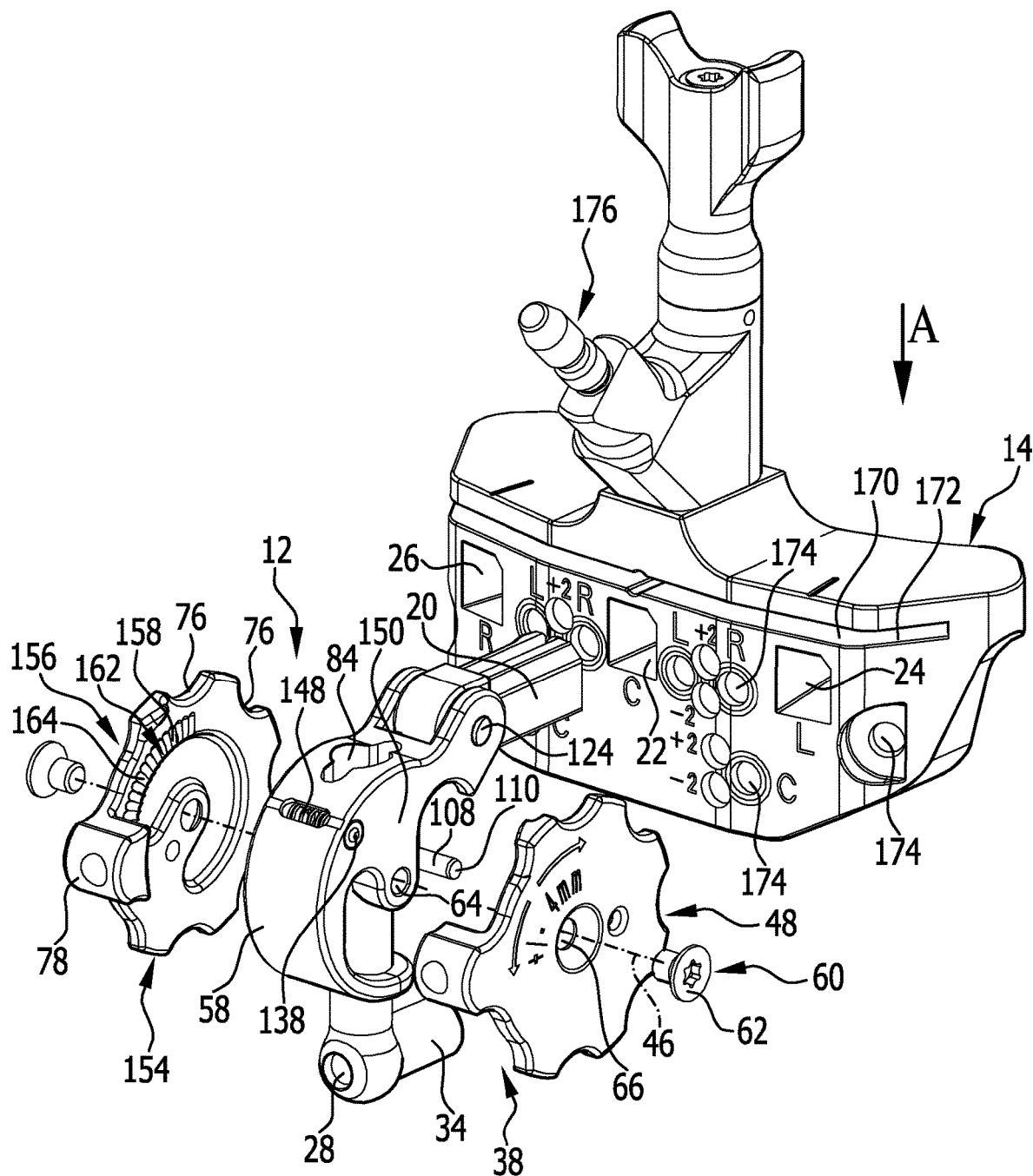
Figure 3:
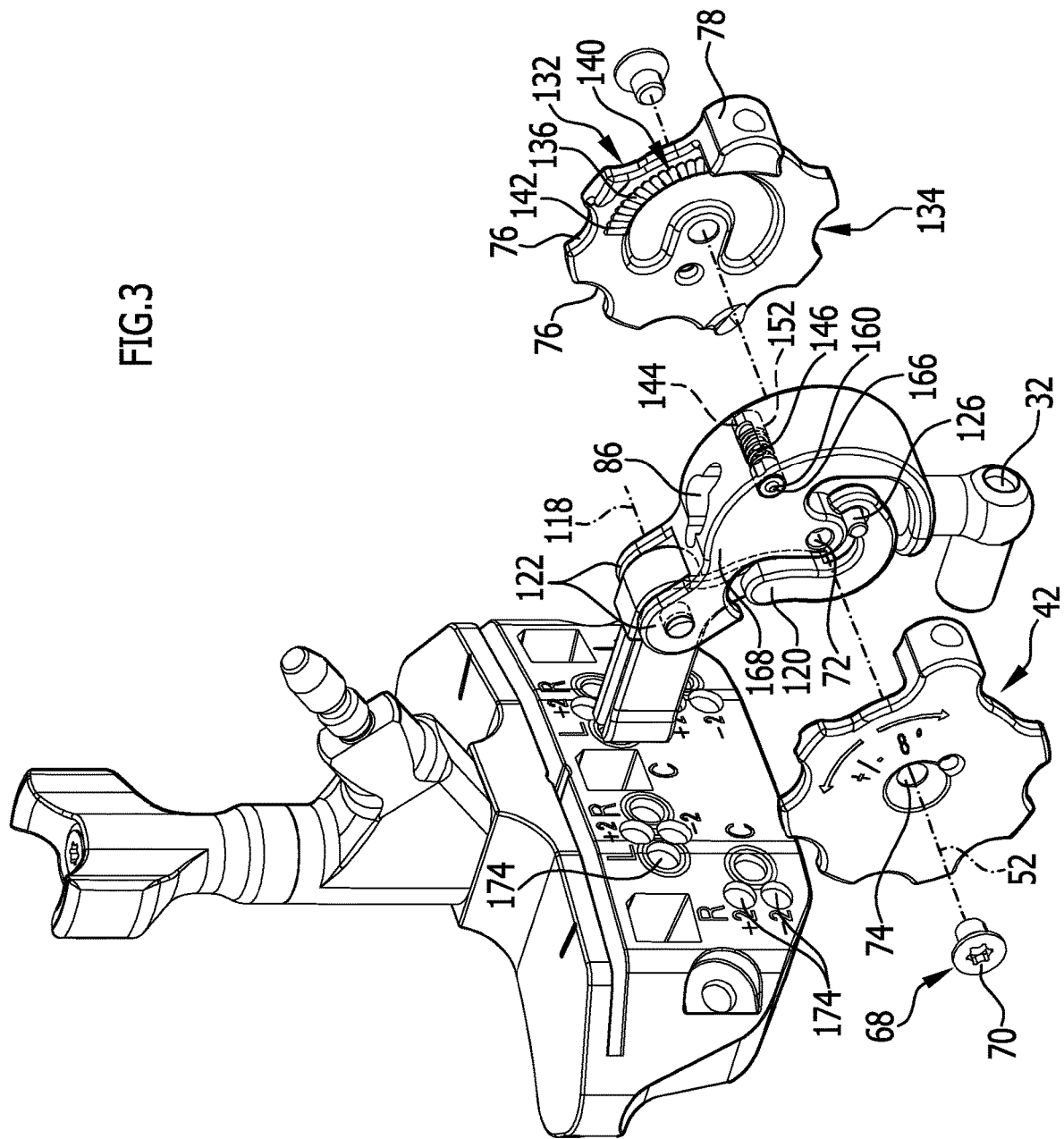
Figure 4:
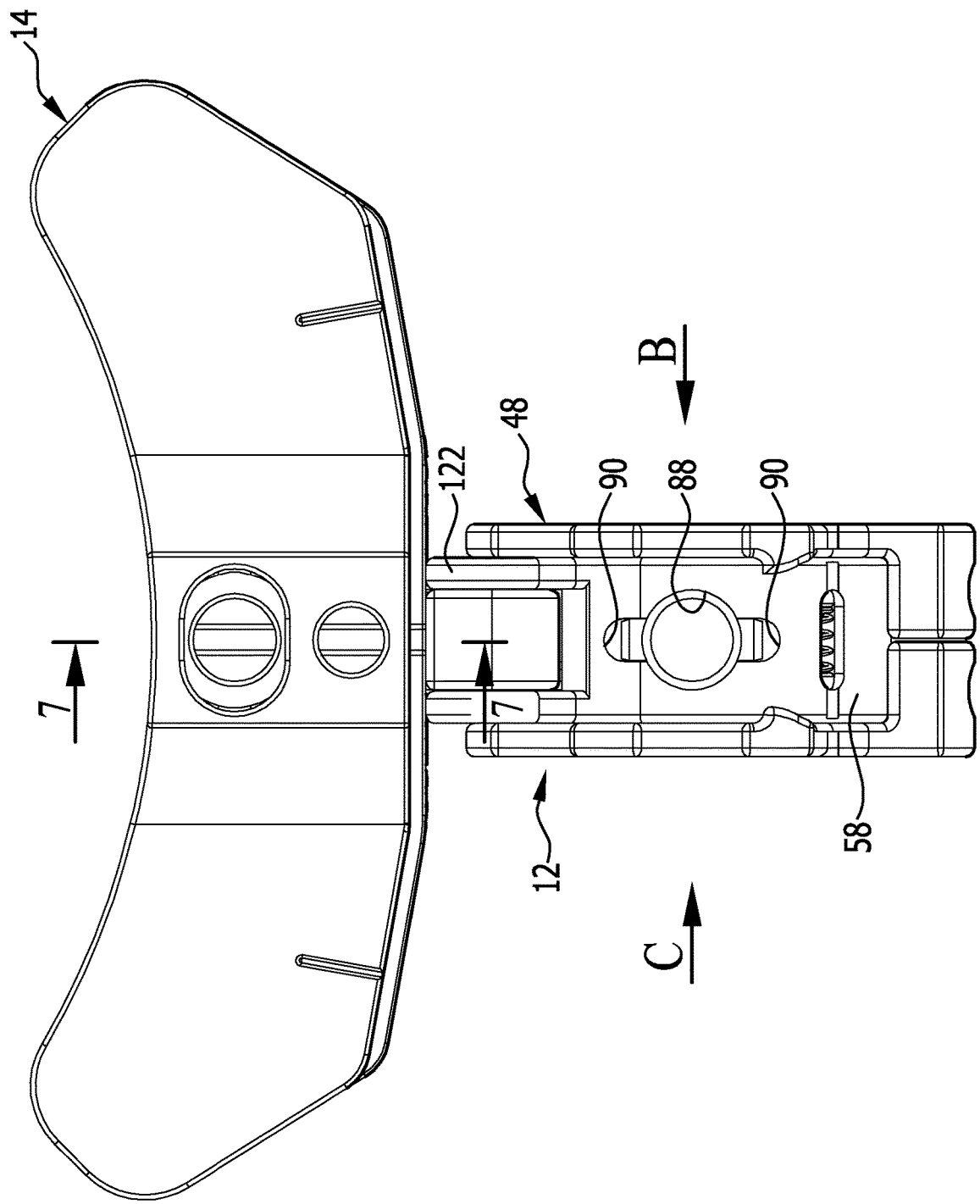
Figure 5:
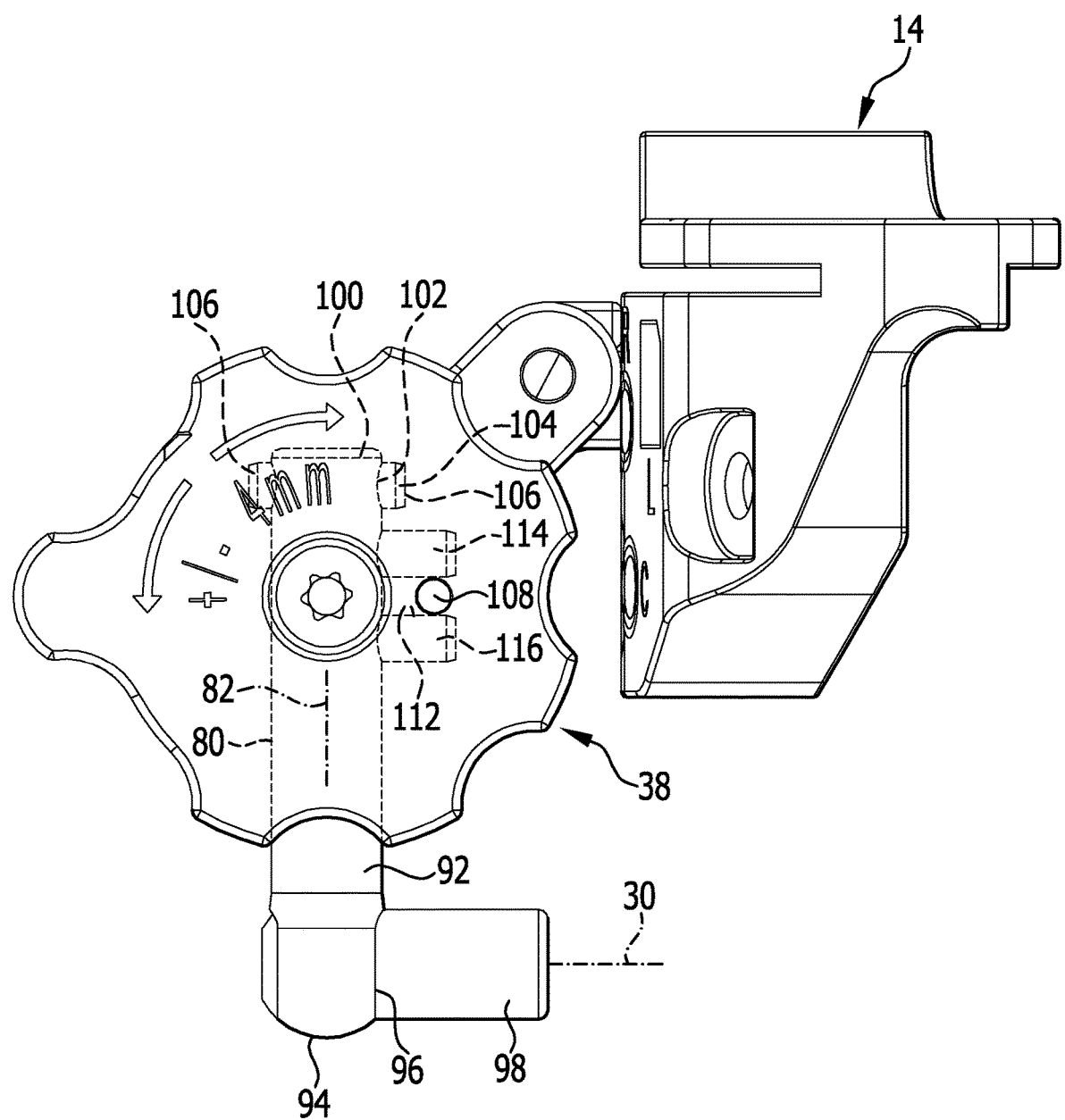
Figure 6:
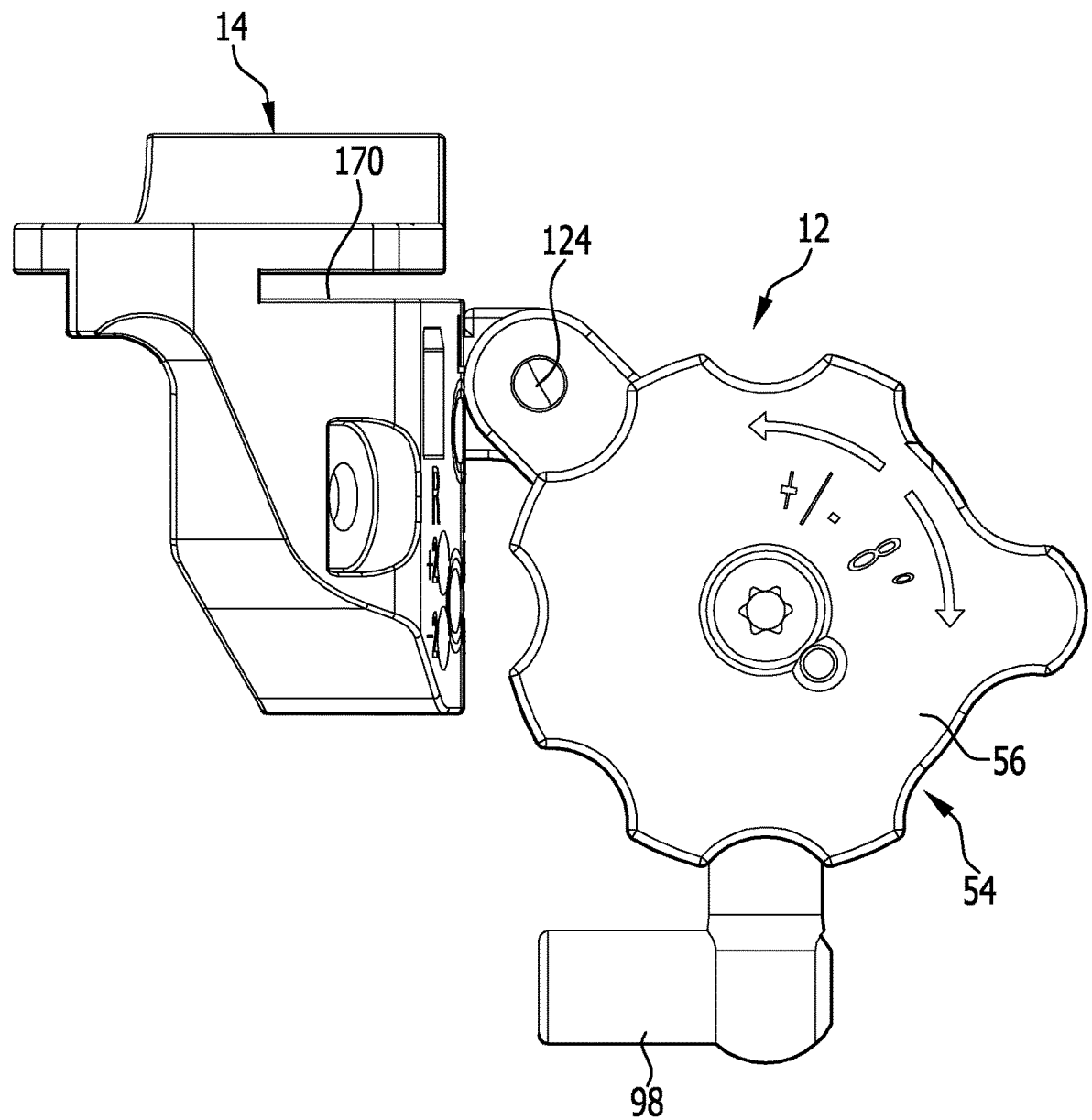
Figure 7:
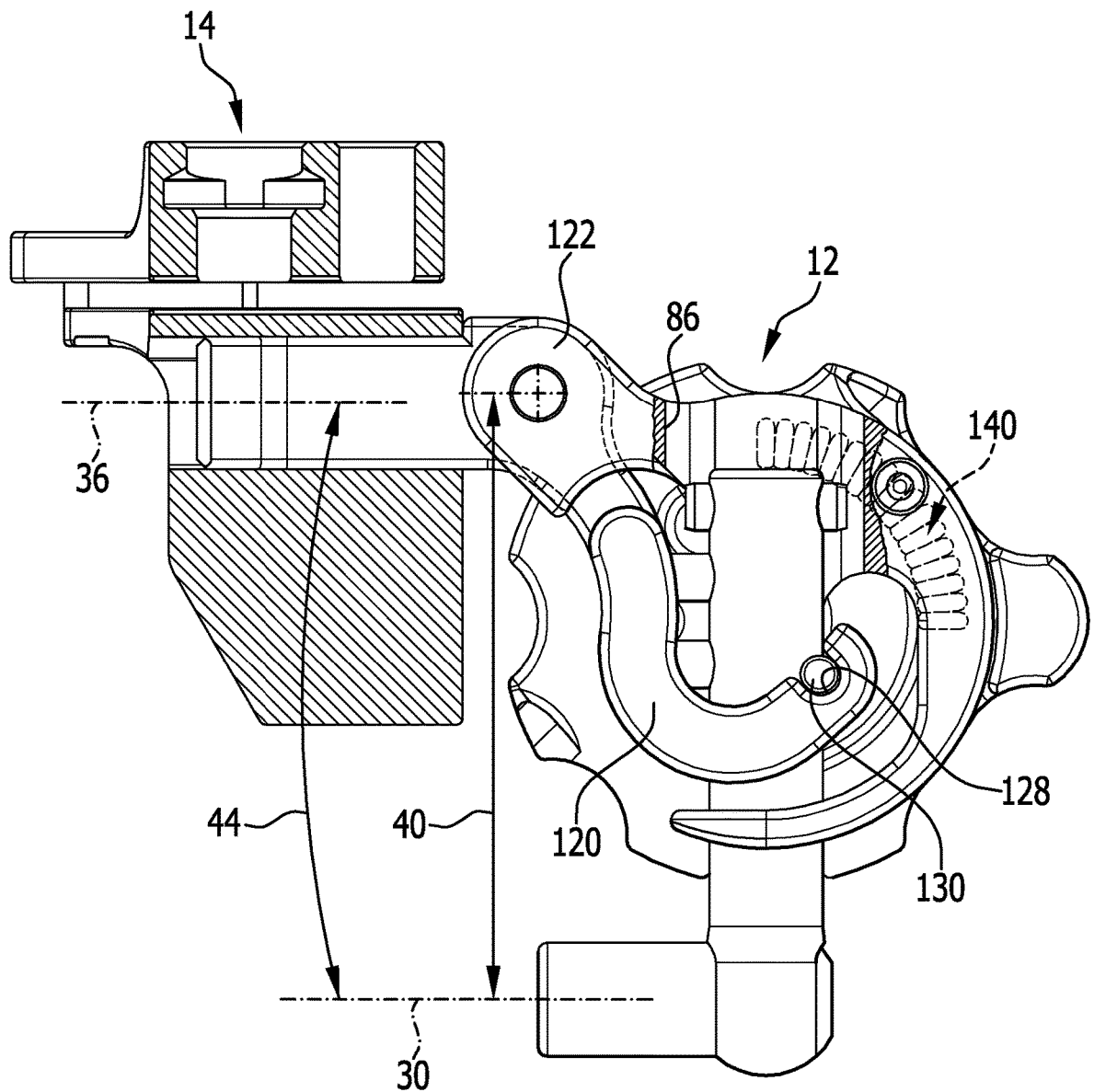

The foregoing summary and the following description may be better understood in conjunction with the drawing figures, of which:

FIG. 1: shows a schematic perspective total view of a medical sawing template system that is fixed to a tibia;

FIG. 2: shows a partially perspective exploded depiction of the sawing template system from FIG. 1;

FIG. 3: shows a further perspective view of the arrangement from FIG. 2;

FIG. 4: shows a view of the arrangement from FIG. 2 in the direction of the arrow A;

FIG. 5: shows a view of the arrangement from FIG. 4 in the direction of the arrow B;

FIG. 6: shows a view of the arrangement from FIG. 4 in the direction of the arrow C; and FIG. 7: shows a sectional view along line 7-7 in FIG. 4.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical sawing template system, comprising an aligning apparatus for aligning a medical sawing template relative to a human or animal bone, which aligning apparatus comprises at least one fastening element receptacle for a fastening element fixable in bone, a first coupling member which is coupleable or coupled to a sawing template, a distance-changing device for varying a distance between the fastening element receptacle and the first coupling member, and an angle-changing device for varying an angle between the fastening element receptacle and the first coupling member, wherein at least one of the distance-changing device comprises a distance-setting member which is rotatable about a distance-setting member rotational axis, and the angle-changing device comprises an angle-setting member which is rotatable about an angle-setting member rotational axis.

With an aligning apparatus of that kind, it is possible in particular to align a sawing template coupled thereto in a highly precise manner when, for example, the aligning apparatus is fixed on a bone with a bone fastening element which engages into the at least one fastening element receptacle of the aligning apparatus. By rotating the distance-setting member, the first coupling member and a sawing template coupled or connected thereto may thus be adjusted in a height, for example. An inclination of a guide perforation of the sawing template may in particular be changed in a simple manner by the angle-setting member being rotated. For example, the distance-setting member and/or the angle-setting member may be configured in the form of setting wheels. The latter may be provided with scales, for example, in order to thus make it easily visible to a surgeon in what way he/she moved the first coupling member and the sawing template, respectively, or adjusted the inclination thereof.

The sawing template system may be configured in a particularly simple and compact manner if the distance-setting member rotational axis defines the angle-setting member rotational axis. Both rotational axes thus coincide. These are to be understood mathematically, and not as mechanical axes, like, for example, bearing axles or the like.

In order to enable a setting of a position and/or inclination of the first coupling member that is as individual as possible, it is advantageous if the distance-changing device and the angle-changing device are actuatable independently of each other. For example, this may be enabled in such a way that the distance-setting member and the angle-setting member are arranged or formed so as to be rotatable independently of each other.

It is advantageous for a handling of the sawing template system if the distance-setting member is configured in the form of a setting wheel.

It is further favorable if the angle-setting member is configured in the form of a setting wheel. It may be rotated in a simple manner by a surgeon for setting an angle of inclination of the sawing template relative to a bone on which the sawing template system in arranged.

In accordance with a further preferred embodiment of the invention, provision may be made for the aligning apparatus to comprise a base body on which the distance-setting member and the angle-setting member are rotatably mounted or held. Providing such a base body enables a particularly compact structure of the sawing template system. In particular, an open construction of the base body may be provided, which enables a good cleanability of the sawing template system.

It is favorable if a distance-setting member bearing element is associated with the distance-setting member and if an angle-setting member bearing element is associated with the angle-setting member. By means thereof, the distance-setting member and the angle-setting member may be rotatably mounted or held on the base body in a simple and secure manner.

The sawing template system may be configured in a particularly simple and inexpensive manner if the distance-setting member bearing element and/or the angle-setting member bearing element are configured in the form of a bearing pin or a screw. For example, the distance-setting member and the angle-setting member may have perforations for accommodating the bearing pin or a screw, and by means of the same are fixed on the base body in such a way that they are still rotatable relative to the base body. In particular, the distance-setting member bearing element and the angle-setting member bearing element are arranged and formed in such a way that the distance-setting member and the angle-setting member are mounted so as only to be rotatable about the distance-setting member rotational axis and the angle-setting member rotational axis, respectively, but are not able to be displaced axially in parallel thereto.

The distance-setting member may be rotatably mounted on the base body in a simple manner if the distance-setting member bearing element is arranged or formed on the base body or on the distance-setting member.

It is further advantageous if the angle-setting member bearing element is arranged or formed on the base body or on the angle-setting member. The angle-setting member may thus be rotatably mounted on the base body in a simple manner.

It is favorable if the distance-setting member and/or the angle-setting member have at least one recess pointing in radial direction away from the distance-setting member rotational axis and/or at least one projection pointing in radial direction away from the distance-setting member rotational axis. The recesses may be configured in particular in the form of concave depressions which improve haptics for a surgeon upon actuation, i.e. when rotating the distance-setting member and the angle-setting member, respectively.

Providing at least one projection which projects in radial direction additionally has the advantage that a surgeon is thus also able to easily see in which direction he/she rotated the distance-setting member and the angle-setting member, respectively. The attachment of a lever may be made possible by an optional recess on the at least one projection, as a result of which the haptics for the surgeon upon actuation may be improved even further.

In accordance with a further preferred embodiment of the invention, provision may be made for the distance-changing device to comprise a sliding element which is displaceably mounted on the base body, defines a sliding element longitudinal axis, and which is arranged or formed cooperating directly or indirectly with the distance-setting member in such a way that the sliding element is displaceable in the direction of the sliding element longitudinal axis by rotating the distance-setting member about the distance-setting member rotational axis. The aligning apparatus may be configured particularly compactly if the distance-setting member and the sliding element are configured to directly cooperate with each other. Elaborate gearing construction may thus be avoided.

In order to be able to ensure a defined orientation of the sawing template upon a displacement of the sliding element, it is favorable if the sliding element is guided on the base body so as to be non-rotatable in relation to the sliding element longitudinal axis.

In order to be able to specify a movement the sliding element in a defined manner, it is advantageous if the base body comprises a sliding element guide in which the sliding element is moveably guided.

The base body may be configured in a simple manner if the sliding element guide is configured in the form of a recess or perforation.

The sliding element guide preferably comprises a non-round cross section. An anti-rotation means for the sliding element relative to the base body may thus be formed in a simple manner, such that said sliding element cannot be rotated about the sliding element longitudinal axis.

It is advantageous if the distance-changing device comprises a sliding catch arranged eccentrically to the distance-setting member rotational axis, if the sliding catch is arranged or formed on the distance-setting member and is moveably in engagement with the sliding element, or if the sliding catch is arranged or formed on the sliding element and is moveably in engagement with the distance-setting member. This proposed design enables in a simple manner a direct cooperation of the distance-setting member and the sliding element by way of the sliding catch.

The aligning apparatus may be configured in a particularly simple and compact manner if the sliding catch is configured in the form of a pin and if a pin longitudinal axis of the pin runs parallel or substantially parallel to the distance-setting member rotational axis.

It is further advantageous if the sliding catch dips into a corresponding guide recess for transmitting a drive force from the distance-setting member to the sliding element. For example, the guide recess may be arranged or formed on the sliding element if the sliding catch is arranged or formed on the distance-setting member. The guide recess may be formed in particular by two guide pins which are aligned in parallel to each other and which are spaced apart from each other, such that the sliding catch is able to engage between them. A distance between the guide pins preferably corresponds roughly to a diameter of the sliding catch, such that a transmission of force is possible here that is as free of play as possible.

The sliding element longitudinal axis preferably runs transversely, in particular perpendicularly, to the distance-setting member rotational axis. The aligning apparatus may thus be configured in particular in such a way that a rotational direction of the distance-setting member in the clockwise direction is able to bring about a displacement movement of the displacement element in one direction, and a rotation of the distance-setting member in the counterclockwise direction is able to bring about a displacement of the sliding element in the opposite direction.

It is further advantageous if the angle-changing device comprises a pivot element which is mounted on the base body so as to be pivotable about a pivot axis and which is arranged or formed directly or indirectly cooperating with the angle-setting member in such a way that the pivot element is pivotable about the pivot axis by rotating the angle-setting member about the angle-setting member rotational axis. In particular, a particularly compact structure of the aligning apparatus may thus be achieved if, for example, the angle-setting member and the pivot element directly cooperate. A complicated redirecting gearing may thus be foregone.

Forces for pivoting the pivot element may be transmitted in a particularly simple manner if the pivot axis runs parallel to the angle-setting member rotational axis.

The first coupling member is preferably arranged or formed on the pivot element. In particular, the first coupling may be formed as one piece with the pivot element. This arrangement makes it possible in particular to configure the aligning apparatus in such a way that an alignment of the first coupling member set with the angle-changing device is maintained when the sliding element is displaced relative to the base body with the distance-changing device.

It is favorable if the first coupling member defines a coupling member longitudinal axis and if the coupling member longitudinal axis runs transversely to the sliding element longitudinal axis. Thus in particular a height adjustment may be separated from an inclination adjustment in simple manner.

A coupling of the aligning apparatus to a sawing template is made particularly simple in particular if the coupling member longitudinal axis runs transversely, in particular perpendicularly, to the pivot axis.

It is favorable if the base body comprises two bearing jaws, if the pivot element is mounted between the bearing jaws on a bearing pin held on the bearing jaws, or if the bearing jaws are mounted on two bearing projections projecting on the pivot element. In this way, the pivot element may be pivotably mounted on the base body in a simple and compact manner.

A particularly compact configuration of the aligning apparatus may be achieved in particular by the bearing pin or the bearing projections defining the pivot axis.

It is further favorable if the angle-changing device comprises a pivot catch arranged eccentrically to the angle-setting member rotational axis, if the pivot catch is arranged or formed on the angle-setting member and is moveably in engagement with the pivot element, or if the pivot catch is arranged or formed on the pivot element and is moveably in engagement with the angle-setting member. This configuration makes it possible in particular to transmit an actuating force, which is introduced via the angle-setting member, via the pivoting catch directly to the pivot element in order to change an alignment of the first coupling member, in particular the angle between the fastening element receptacle and the first coupling member. Eccentric means in particular that a position of the pivoting catch is at a distance from the angle-setting member rotational axis.

The aligning apparatus may be configured in a particularly simple and inexpensive manner if the sliding catch is configured in the form of a pin and if a pin longitudinal axis of the pin runs parallel or substantially parallel to the angle-setting member rotational axis. In particular, the pin longitudinal axis may run parallel to the pivot axis.

A transmission of force between the angle-setting member and the pivot element may be achieved in a particularly simple manner if the pivoting catch engages into a corresponding pivoting catch guide recess for transmitting a drive force from the angle-setting member to the pivot element.

The pivot axis preferably runs parallel or substantially parallel to the distance-setting member rotational axis. This enables a particularly compact structure of the aligning apparatus.

In order to be able to carry out an angle adjustment with particularly small forces, it is favorable if a distance of the pivot axis from the angle-setting member rotational axis is greater than a distance of the pivoting catch from the angle-setting member rotational axis.

It is advantageous if a distance of the sliding catch from the distance-setting member rotational axis is greater than a distance of the pivoting catch from the distance-setting member rotational axis.

A distance of the pivot axis from the angle-setting member rotational axis is preferably greater than a distance of the pivot axis from the pivoting catch. The pivot element may thus be pivoted with particularly small pivoting forces.

It is favorable if the distance-changing device is configured to vary the distance between the fastening element receptacle and the first coupling member in discrete distance steps. For example, the distance-changing device may thus be configured in such a way that it maintains its set position. In addition, a surgeon may in particular also obtain feedback on a number of distance-changing steps made by him/her for changing the distance.

In order for a surgeon to be able to set the distances in a defined manner, it is advantageous if the discrete distance steps are the same size or substantially the same size.

The distance-changing device preferably comprises a distance step-setting device for setting discrete distances between the fastening element receptacle and the first coupling member. Discrete distance steps may be specified with the distance step-setting device.

It is advantageous if the distance step-setting device is configured in the form of a distance latching mechanism comprising mutually cooperating first and second distance latching members, and if the first and second distance latching members are in engagement at discrete distances between the fastening element receptacle and the first coupling member. Such a distance latching mechanism makes it possible in particular to give a surgeon a haptic feedback when changing a distance.

The distance step-setting device may be configured in a simple manner if the first and second distance latching members are arranged or formed on the distance-setting member on the one hand and on the base body on the other hand.

A plurality of first distance latching members is preferably configured in the form of teeth forming a distance toothing. The distance toothing may be configured, e.g., in the form of a linear toothing or an arc toothing.

A particularly compact configuration of the aligning apparatus may be achieved if the distance toothing is arranged or formed concentrically surrounding the distance-setting member rotational axis. The distance toothing may thus, for example, securely cooperate with a second latching member arranged at a constant distance from the distance-setting member rotational axis.

It is advantageous if a second distance latching member is configured in the form of a distance latching body which is deflectable out of a base position against a biasing element. The distance latching body may thus be moved counter to the action of the biasing element and successively engage between adjacent teeth of the distance toothing when rotating the distance-setting member.

A particularly compact structure of the aligning apparatus is made possible in particular by a direction of action of the biasing element running parallel or substantially parallel to the distance-setting member rotational axis.

It is advantageous if the first distance latching members are arranged or formed projecting from the distance-setting member pointing in the direction toward the base body. In particular, the distance-setting member may comprise or bear the toothing.

In order to easily and securely maintain a set distance, even under load when using a saw template, it is favorable if a distance of the first distance latching members from the distance-setting member rotational axis is greater than a distance of the sliding catch from the distance-setting member rotational axis.

In accordance with a further preferred embodiment of the invention, provision may be made for the angle-changing device to comprise an angle step-setting device for setting discrete angles between the fastening element receptacle and the first coupling member. This makes it possible in a simple manner for a surgeon to change the angle in discrete steps, for example in steps of 1°, in order to thus obtain an optimal and precise adjustment and positioning of the sawing template.

It is favorable if the angle step-setting device is configured in the form of an angle latching mechanism comprising mutually cooperating first and second angle latching members, and if the first and second angle latching members are in engagement at discrete angles between the fastening element receptacle and the first coupling member. Thus, discrete angle steps may be set by a surgeon in a simple manner.

The aligning apparatus may be configured in a simple and compact manner if the first and second angle latching members are arranged or formed on the angle-setting member on the one hand and on the base body on the other hand.

In order to be able to specify a plurality of discrete angle steps, it is favorable if a plurality of first angle latching members is configured in the form of teeth forming an angle toothing. Such an angle toothing may in particular cooperate with one single second angle latching member which is able to engage between adjacent teeth of the angle toothing and thus specify defined angular positions.

The angle toothing is preferably arranged or formed concentrically surrounding the angle-setting member rotational axis. This enables a simple and compact structure of the angle-changing device.

It is favorable if a second angle latching member is configured in the form of an angle latching body which is deflectable out of a base position against a biasing element. In particular a ball pressure piece may thus be formed if the angle latching body is configured in the form of a ball and the biasing element is configured in the form of a compression spring.

A particularly compact structure of the aligning apparatus may be achieved in particular by a common biasing element being associated with the second distance latching member and the second angle latching member. Thus effectively a double ball pressure piece may be formed which cooperates with the angle toothing on the one hand and with the distance toothing on the other hand. The biasing element may be arranged in particular in a recess, for example in a bore, of the base body.

A direction of action of the biasing element preferably runs parallel or substantially parallel to the angle-setting member rotational axis. Maximal latching forces upon cooperation of the first and second angle latching members may thus be achieved. The same also applies to the biasing element which cooperates with the second distance latching member.

It is advantageous if the first angle latching members are arranged or formed projecting from the angle-setting member pointing in the direction toward the base body. They are thus able to cooperate in a simple manner with a second angle latching member projecting out of the base body.

It is favorable if a distance of the first angle latching members from the angle-setting member rotational axis is greater than a distance of the pivoting catch from the angle-setting member rotational axis. Thus in particular a set angle may be easily and securely maintained, even under load when using a sawing template.

It is further advantageous if a fastening element receptacle is arranged or formed on the sliding element. In particular, the fastening element receptacle may be configured in the form of a perforation that is rotationally symmetrical in cross section, for example in the form of a bore. Such a configuration makes it possible in particular to pivot the sliding element and thus the entire aligning apparatus about a rotational or pivot axis defined by the fastening element receptacle. Thus a coarse positioning of the sawing template on the bone may first be carried out. A fine adjustment then takes place with the distance-changing device and with the angle-changing device. In addition, this arrangement of the fastening element receptacle makes it possible to carry out the changing of the distance and the angle in series, as it were. The base body may be displaced relative to the sliding element and thus relative to the fastening element receptacle by means of the distance-changing device. Furthermore, the first coupling member may be pivoted relative to the base body and thus also to the fastening element receptacle, independently of a change in distance. Further, the fastening element receptacle may be configured in the form of an elongated sleeve in order to improve a stability of a connection between the sliding element and the fastening element. In particular, a play between the fastening element passing through the fastening element receptacle and the sliding element may thus be minimized.

It is favorable if the medical sawing template system comprises at least one fastening element for anchoring in a bone. A fastening element may in particular serve for arranging and positioning the aligning apparatus on the bone. Said fastening element is then guided through the fastening element receptacle of the aligning apparatus, which may be arranged in particular on the sliding element. Further fastening elements may serve in particular to fix the sawing template, brought by a surgeon into a desired position, on the bone before he/she places a saw cut, guided by the sawing template, on the bone with a surgical saw.

The sawing template system may be fixed on a bone in a simple manner if the at least one fastening element is configured in the form of a bone pin or in the form of a bone screw. In particular, the fastening element may have cylindrical sections which may be rotatably guided in the fastening element receptacle of the aligning apparatus.

It is favorable if the sawing template system comprises a sawing template with at least one guide perforation for a saw blade. The guide perforation may be configured in particular in the form of a guide slot. The sawing template may have two, three or more guide slots.

In order to be able to fix the sawing template on a bone in a defined manner, it is favorable if the sawing template comprises at least one sawing template fastening element receptacle for accommodating at least one fastening element. Preferably at least two sawing template fastening element receptacles are provided, which define longitudinal axes that do not run parallel to each other.

Furthermore, it may be advantageous if the sawing template comprises a second coupling member for bringing into engagement with the first coupling member. The sawing template may thus be separated from the aligning apparatus as required. In particular, the aligning apparatus may thus be released from the sawing template when the sawing template is fixed in a defined position on the bone with corresponding fastening elements. The aligning apparatus, which is then interfering, may be removed before placing a saw cut in order to clear the surgical site as well as possible.

It is further favorable if the sawing template is non-releasably connected to the first coupling member or is formed as one piece with the first coupling member. Thus, a particularly play-free connection between the fastening element receptacle of the aligning apparatus and the sawing template may be formed.

In order to be able to determine a position of the sawing template in space as precisely as possible, it is advantageous if the sawing template comprises at least one first coupling element for bringing into engagement with a second coupling element of a medical referencing unit. The medical referencing unit may be configured in particular to be detected by a medical navigation system, in particular a detecting device thereof, in order to be able to identify the position and/or orientation of the sawing template in space. In particular, an alignment of the sawing template on the bone may thus be carried out by a surgeon with the support of navigation.

It is advantageous if the sawing template system comprises a medical referencing unit, the position and/or orientation in space of which is determinable with a medical navigation system. As described, a sawing template may thus be positioned on the bone and aligned relative thereto with the support of navigation in order to prepare the bone faces required for the implantation of joint implants.

In accordance with a further preferred embodiment of the invention, provision may be made for the referencing unit to be arranged or formed on the sawing template, or for the referencing unit to comprise a second coupling element for bringing into engagement with the first coupling element of the sawing template in a coupling position. In particular, the referencing unit may thus be removed from the sawing template when the latter is positioned and fixed on the bone in the desired manner. A surgeon thus has more space available at the surgical site.

A medical sawing template system, designated as a whole with the reference numeral 10, is schematically depicted in FIG. 1. It comprises an aligning apparatus 12 and optionally a sawing template 14, as well as optionally one or a plurality of fastening elements 16 for fixing to a bone 18.

The fastening element 16 may in particular be configured in the form of a bone pin or a bone screw.

The aligning apparatus 12 comprises a first, substantially cuboidal coupling member 20 which forms an interface for temporarily coupling to the sawing template 14. The pin-shaped coupling member 20 comprises a leaf spring, not depicted, in order to bring it into engagement in a force- and/or positive-locking manner with a second coupling member 22 formed on the sawing template 14. The second coupling member 22 is configured in the form of a cuboidal recess.

Optionally, further second coupling members 24 and 26 may be formed on the sawing template 14 in order to couple the sawing template 14 to the aligning apparatus 12 in different relative positions.

The aligning apparatus 12 further comprises a fastening element receptacle 28. The latter is configured in the form of a bore 32 of a guide sleeve 34, which defines a longitudinal axis 30.

The first coupling member 20 defines a coupling member longitudinal axis 36.

The aligning apparatus 12 further comprises a distance-changing device 38 for varying a distance 40 between the fastening element receptacle 28 and the first coupling member 20.

The aligning apparatus 12 further comprises an angle-changing device 42 for varying an angle 44 between the fastening element receptacle 28 and the first coupling member 20, namely in particular for setting the angle 44 that is enclosed by the longitudinal axis 30 and the coupling member longitudinal axis 36.

For changing the distance 40, the distance-changing device 38 comprises a distance-setting member 46 which is rotatable about a distance-setting member rotational axis 46 and is configured in the form of a setting wheel 50.

The angle-changing device 42 comprises an angle-setting member 54 which is rotatable about an angle-setting member rotational axis 52 and is also configured in the form of a setting wheel 56.

In the case of the aligning apparatus 12 depicted in the Figures, the distance-setting member rotational axis 46 and the angle-setting member rotational axis 52 coincide. In other words, the distance-setting member rotational axis 46 defines the angle-setting member rotational axis 52.

The distance-changing device 38 is actuatable independently of the angle-changing device 42.

The aligning apparatus 12 comprises a substantially half-moon-shaped base body on which both the distance-setting member 48 and the angle-setting member 54 are rotatably mounted or held.

A distance-setting member bearing element 60 in the form of a screw 62 is associated with the distance-setting member 48, the shank of which screw 62 is provided with an external thread that corresponds to an internal thread of a threaded bore 64 on the base body 58. The shank of the screw 62 passes through a perforation 66 on the setting wheel 50, so that the setting wheel 50 is able to be rotatably fastened to the base body 58 by screwing the shank of the screw 62 into the threaded bore 64.

In an analogous manner, an angle-setting member bearing element 68 in the form of a screw 70 is associated with the angle-setting member 54, the shank of which screw 70, which is provided with an external thread, may be screwed to a threaded bore 72 on the base body 58. The setting wheel 56 is provided with a perforation 74, so that it may be rotatably connected to the base body 58 correspondingly to the setting wheel 50.

Both the distance-setting member 48 and the angle-setting member 54 have a plurality of recesses 76 pointing in radial direction away from the distance-setting member rotational axis 46, so that a sort of outer toothing of the setting wheels 50 and 56 is formed.

Furthermore, formed on each setting wheel 50, 56 is a projection 78 which projects pointing in radial direction away from the distance-setting member rotational axis 46. The two projections 78 also extend in parallel to the distance-setting member rotational axis 46, each point toward each other, and also each have a bore which runs perpendicularly to the distance-setting member rotational axis 46 and is temporarily coupleable to a lever, for example.

The distance-changing device 38 further comprises a sliding element 80 which defines a sliding element longitudinal axis 82. The sliding element longitudinal axis 82 runs perpendicularly to the longitudinal axis 30.

A sliding element guide 84 is formed on the base body 58 in the form of a perforation 86 which has a non-round cross section. The perforation 86 is formed by a bore 88 defining the sliding element longitudinal axis 82, and by two cutouts 90 which are formed pointing in radial direction away from the sliding element longitudinal axis 82 and are diametrically opposed to each other in relation to the sliding element longitudinal axis 82.

The sliding element 80 is configured in the form of a cylindrical bolt 92 which is provided with a bore 96 adjacent to a free end 94, into which bore 96 a sleeve 98 is inserted that is provided with the bore 32 for forming the fastening element receptacle 28.

Formed adjacent to a second end 100 pointing away from the end 94 is a further bore 102 into which a guide pin 104 is inserted, the free ends 106 of which, pointing away from each other, protrude laterally over the bolt 92. A longitudinal axis of the guide pin 104 is aligned in parallel to the longitudinal axis 30. The ends 106 engage into the lateral cutouts 90, so that the sliding element 80 is displaceable in the sliding element guide in parallel to the sliding element longitudinal axis 82 and is secured against a rotation about the latter.

The distance-changing device 38 further comprises a sliding catch 108 which is arranged on the distance-setting member 48 eccentrically in relation to the distance-setting member rotational axis 46. The sliding catch 108 is configured in the form of a pin 110, the pin longitudinal axis of which runs parallel to the distance-setting member rotational axis 46.

The sliding catch 108 engages into the guide recess 112. The latter is formed by two pins 114 and 116 which have a distance from each other that corresponds to a diameter of the pin 110.

The pins 114 and 116 are inserted in bores or blind holes on the sliding element 80 and are aligned such that the longitudinal axes thereof run parallel to the longitudinal axis 30. In this way, the sliding element guide 80 is moveably in engagement with the sliding catch 108, so that a drive force may be transmitted from the distance-setting member 48 to the sliding element 80 for moving the same according to the principle of eccentricity. By rotating the setting wheel 50, the sliding catch 108 is rotated about the distance-setting member rotational axis 46 so that it is able to displace the sliding element 80 in the sliding element guide 84.

The sliding element longitudinal axis 82 runs perpendicularly to the distance-setting member rotational axis 46.

In the described way, the distance-setting member 48 is configured to cooperate directly with the sliding element 80.

The angle-changing device 42 comprises a pivot element 120 which is mounted on the base body 58 so as to be pivotable about a pivot axis 118 and which is configured in the form of a pivot lever.

The pivot axis 118 runs parallel to the angle-setting member rotational axis 52.

The first coupling member 20 is formed on the pivot element 120 and forms a free end thereof. The coupling member longitudinal axis 36 runs perpendicularly to the pivot axis 118, namely independently of how the pivot element 120 is pivoted relative to the base body 58 about the pivot axis 118.

On the base body 58, two flat bearing jaws 122 project in parallel to each other, between which bearing jaws 122 the pivot element 120 is mounted on a bearing pin 124 held on the bearing jaws 122. The bearing pin 124 defines the pivot axis 118.

The angle-changing device 42 comprises a pivoting catch 126 which is arranged eccentrically on the angle-setting member 24 in relation to the angle-setting member rotational axis 52. The pivoting catch 126 is configured in the form of a pin 128, the pin longitudinal axis of which runs parallel to the angle-setting member rotational axis 52.

The pivoting catch 126 is moveably in engagement with the pivot element 120, namely by the pivoting catch 126 engaging into a corresponding pivoting catch guide recess 130 for transmitting a drive force from the angle-setting member to the pivoting element 120 according to the principle of eccentricity.

The pivot axis 118 also runs parallel to the distance-setting member rotational axis 46 and thus also parallel to the angle-setting member rotational axis 52.

A distance of the pivot axis 118 from the angle-setting member rotational axis 52 is greater than a distance of the pivoting catch 108 or the longitudinal axis thereof from the angle-setting rotational axis 52.

Furthermore, a distance of the sliding catch 108 or the longitudinal axis thereof from the distance-setting member rotational axis 46 is greater than a distance of the pivoting catch 108 from the distance-setting member rotational axis 46.

In addition, a distance of the pivot axis 118 from the angle-setting member rotational axis 52 is greater than a distance of the pivot axis 118 from the pivoting catch 108 or the longitudinal axis thereof.

When the setting wheel 56 is rotated about the angle-setting member rotational axis 52, the pivoting catch 126 catches the pivot lever and pivots the same about the pivot axis 118. The angle 44 between the coupling member longitudinal axis 36 and the longitudinal axis 30 thereby changes. In other words, an inclination of the first coupling member 20 relative to the longitudinal axis 30 or to the fastening element receptacle 28 is set or changed by turning or rotating the angle-setting member 54.

Furthermore, the aligning apparatus 12 is configured in such a way that the distance 40 may be varied in discrete distance steps with the distance-changing device. Said distance steps may in particular be the same size or substantially the same size. For example, the distance steps may be 0.5 mm, 1 mm, or 1.5 mm.

The distance-changing device 38 comprises a distance step-setting device 132 for setting discrete distances 40 between the fastening element receptacle 28 and the first coupling member 20.

The distance step-setting device 132 is configured in the form of a distance latching mechanism 134 and comprises mutually cooperating first distance latching members 136 and a second distance latching member 138. The first and second distance latching members 136, 138 are in engagement at discrete distances 40.

The distance latching mechanism 134 comprises a plurality of first distance latching members 136 which are configured in the form of teeth 142 forming a distance toothing 140. The first distance latching members 136 are formed or arranged on the distance-setting member 48, the second distance latching member is arranged or formed on the base body 58.

The distance toothing 140 is arranged or formed concentrically surrounding the distance-setting member rotational axis 46 and extends roughly over an angular range of 90° in relation to the distance-setting member rotational axis 46.

The second distance latching member 138 is configured in the form of a spherical distance latching body 144 which is able to be deflected out of a base position, in which it projects over a side face 150 of the base body 58 that points in the direction toward the setting wheel 50, against the action of a biasing element 146 which is configured in the form of a compression spring 148.

The biasing element 146 is inserted into a transverse bore 152 of the base body 58. A longitudinal axis of the transverse bore 152 runs parallel to the distance-setting member rotational axis 46. Thus the direction of action of the biasing element 146 also runs parallel to the distance-setting member rotational axis 46.

The teeth 142 are arranged or formed projecting from the distance-setting member 48 pointing in the direction toward the base body 58.

A distance of the first distance latching members 136 from the distance-setting member rotational axis 46 is greater than a distance of the sliding catch 108 from the distance-setting member rotational axis 46.

The angle 44 may also be adjusted in discrete angle steps with the angle-changing device 42. In order to make this possible, the angle-changing device 42 comprises an angle step-setting device 154 for setting discrete angles 44 between the fastening element receptacle 28 or the longitudinal axis 30 and the first coupling member 20 or the coupling member longitudinal axis 36 thereof.

The angle step-setting device 154 is configured in the form of an angle latching mechanism 156. The latter comprises mutually cooperating first angle latching members 158 and a second angle latching member 160. The second angle latching member 160 is in engagement with two angle latching members 158 at discrete angles 44.

The angle step-setting device 154 comprises a plurality of first angle latching members 158 which are formed on the setting wheel in the form of teeth 164 forming an angle toothing 162. The first angle latching members 158 are thus arranged or formed on the angle-setting member 54.

The second angle latching member 160 is arranged or formed on the base body 58.

The angle toothing 162 is arranged or formed concentrically surrounding the angle-setting member rotational axis 52. It extends over an angular range of about 90° in relation to the angle-setting member rotational axis 52.

The second angle latching member 160 is configured in the form of a spherical angle latching body 166. The latter is held in a base position by the biasing element 146, projecting somewhat over a side face 168 of the base body that points in the direction toward the setting wheel 56. The angle latching body 166 is thus deflectable out of its base position against the action of the biasing element 146.

The first angle latching members 158 are arranged or formed projecting from the angle-setting member 54 pointing in the direction toward the base body 58.

A distance of the first angle latching members 158 from the angle-setting member rotational axis 52 is greater than a distance of the pivoting catch 126 from the angle-setting member rotational axis 52.

The sawing template 14 comprises a guide perforation 170 in the form of a guide slot 172 for guiding a saw blade of a surgical saw, which is not depicted in the Figures. In particular, it may hereby be an oscillating saw.

The sawing template 14 may additionally, as depicted for example in the Figures, have a plurality of sawing template fastening element receptacles 174 through which fastening elements, for example bone pins or bone screws, are guidable. Longitudinal axes of the sawing template fastening element receptacles 174 may in particular be configured in parallel or inclined at an angle to each other in the form of bores.

The sawing template 14 may comprise one or a plurality of first coupling elements 176 for bringing into engagement with a second coupling element 178 of a medical referencing unit 180.

The sawing template system 10 may in particular comprise one or a plurality of referencing units 180 of that kind. A position and/or an orientation in space of the referencing unit 180 may be determined in particular with a medical navigation system 182.

In particular, the referencing unit 180 may comprise a plurality of marker elements, preferably at least three, the position in space of which is determinable with the navigation system 182. A position and an orientation of the referencing unit 180 may then be identified with the navigation system 182 from a known relative positioning of the marker elements 184. An orientation and a position in space of the sawing template 14, which is coupled to the referencing unit 180, are thus also determinable.

For placing a saw cut on the bone 18, one may proceed in particular as follows.

The aligning apparatus 12 is first brought into a neutral position. In this position, the setting wheels 50 and 56 are rotated such that they can still be rotated about equally as far in both the clockwise direction and in the counter-clockwise direction. The projections 78 then directly adjoin each other, as is depicted for example in FIG. 1.

The referencing unit 80 is coupled to the sawing template 14 and the sawing template, in turn, to the aligning apparatus 12 by bringing the coupling members 20 and 22 into engagement.

The surgeon may now bring the unit, schematically depicted in FIG. 1, comprising the referencing unit 180, the sawing template 14, and the aligning apparatus 12, up to the bone 18 and have the navigation system 182 display whether he/she has reached the desired cutting position. After this coarse adjustment, the surgeon holds the unit against the bone 18 and fixes it on the bone 18 by inserting the fastening element 16 through the fastening element receptacle 28.

In a next step, the angle 44 is now set with the support of the navigation system 182. For this purpose, the setting wheel 56 is correspondingly rotated until the inclination of the first coupling member 20 and thus also of the guide slot 152 correspond with the preoperatively determined specifications.

Now a resection height may finally be set by varying the distance 40. This is achieved, as described, by rotating the setting wheel 50 in the clockwise direction or in the counterclockwise direction.

The entire unit may now still be rotated about the longitudinal axis defined by the fastening element 16 in order to set a varus-valgus angle. This, too, takes place with the support of the navigation system 182.

When the surgeon has found the desired position of the sawing template 14, he/she fixes the same on the bone 18 with further fastening elements, not depicted in the Figures, by said fastening elements being guided through the sawing template fastening element receptacles 74 and being driven into the bone 18.

When the sawing template 14 is fixed sufficiently immovably on the bone 18, the fastening element 16 may be removed and then also the aligning apparatus 12 removed from the sawing template 14 by the first and second coupling members 20, 22 being brought out of engagement.

The referencing unit 180 may optionally also be separated from the sawing template 14 by bringing the coupling elements 176 and 178 out of engagement.

With the sawing template 14 now positioned and fixed, the surgeon may insert the saw blade of the surgical saw through the guide slot 172 and partially resect the bone 18 for preparing a bone face against which an implant part is to be placed and fixed.

The sawing template system 10 described above makes it possible in particular to achieve an exact positioning with a structure of the aligning apparatus 12 that is as compact as possible. The sawing template system 10 is therefore also suitable in particular for minimally invasive interventions for the implantation of joint endoprostheses.

The implementation of the principle of eccentricity in the aligning apparatus 12 for setting both the angle 44 and the distance 40 makes it possible in particular to completely forgo threaded drives and the like. An exact and self-locking setting both of the distance 40 and of the angle 44 is nonetheless possible, even without having to carry out a plurality of rotations of the setting wheels 50 and 56. A precise adjustment is possible here in particular by means of rotational movements in the range of a circumferential angle of about 90°.

Because the aligning apparatus requires only one single fastening element 60 for the positioning, typically no additional incision, or no incision larger than that which is required anyway for the sawing template 14, is necessary.

REFERENCE NUMERAL LIST 10 sawing template system
12 aligning apparatus
14 sawing template
16 fastening element
18 bone
20 first coupling member
22 second coupling member
24 second coupling member
26 second coupling member
28 fastening element receptacle
30 longitudinal axis
32 bore
34 guide sleeve
36 coupling member longitudinal axis
38 distance-changing device
40 distance
42 angle-changing device
44 angle
46 distance-setting member rotational axis
48 distance-setting member
50 setting wheel
52 angle-setting member rotational axis
54 angle-setting member
56 setting wheel
58 base body
60 distance-setting member bearing element
62 screw
64 threaded bore
66 perforation
68 angle-setting member bearing element
70 screw
72 threaded bore
74 perforation
76 recess
78 projection
80 sliding element
82 sliding element longitudinal axis
84 sliding element guide
86 perforation
88 bore
90 cutout
92 bore
94 end
96 bore
98 sleeve
100 end
102 bore
104 guide pin
106 end
106 sliding catch
110 pin
112 guide recess
114 pin
116 pin
118 pivot axis
120 pivot element
122 bearing jaws
124 bearing pin
126 pivoting catch
128 pin
130 pivoting catch guide recess
132 distance step-setting device
134 distance latching mechanism
136 first distance latching member
138 second distance latching member
140 distance toothing
142 tooth
144 distance latching body
146 biasing element
148 compression spring
150 side face
152 transverse bore
154 angle step-setting device
156 angle latching mechanism
158 first angle latching member
160 second angle latching member
162 angle toothing
164 tooth 166 angle latching body
168 side face
170 guide perforation
172 guidance slot
174 sawing template fastening element receptacle
176 first coupling element
178 second coupling element
180 referencing unit
182 navigation system
184 marker element

What is claimed is:

1. Medical sawing template system, comprising an aligning apparatus for aligning a medical sawing template relative to a human or animal bone, which aligning apparatus comprises at least one fastening element receptacle for a fastening element fixable in bone, a first coupling member which is coupleable or coupled to a sawing template, a distance changing device for varying a distance between the fastening element receptacle and the first coupling member, and an angle-changing device for varying an angle between the fastening element receptacle and the first coupling member, wherein at least one of the distance-changing device comprises a distance-setting member which is rotatable about a distance-setting member rotational axis, and the angle-changing device comprises an angle-setting member which is rotatable about an angle setting member rotational axis, wherein the distance-setting member rotational axis defines the angle-setting member rotational axis.

2. Medical sawing template system in accordance with claim 1, wherein at least one of
   a) the distance-changing device and the angle-changing device are actuatable independently of each other;
   b) the distance-setting member is configured in the form of a setting wheel;
   c) the angle-setting member is configured in the form of a setting wheel;
   d) the aligning apparatus comprises a base body on which the distance-setting member and the angle-setting member are rotatably mounted or held;
   e) a distance-setting member bearing element is associated with the distance-setting member, and wherein an angle-setting member bearing element is associated with the angle-setting member; or a distance-setting member bearing element is associated with the distance-setting member, and wherein an angle-setting member bearing element is associated with the angle-setting member, wherein at least one of
   e1) at least one of the distance-setting member bearing element and the angle-setting member bearing element are configured in the form of a bearing pin or a screw and
   e2) the distance-setting member bearing element is arranged or formed on the base body or on the distance-setting member and
   e3) the angle-setting member bearing element is arranged or formed on the base body or on the angle-setting member, and
   f) at least one of the distance-setting member and the angle-setting member have at least one recess pointing in radial direction away from the distance-setting member rotational axis and at least one projection pointing in radial direction away from the distance-setting member rotational axis.

3. Medical sawing template system in accordance with claim 1, wherein
   a) the aligning apparatus comprises a base body on which the distance-setting member and the angle-setting member are rotatably mounted or held, and wherein the distance-changing device comprises a sliding element which is displaceably mounted on the base body and defines a sliding element longitudinal axis, which sliding element is arranged or formed cooperating directly or indirectly with the distance-setting member in such a way that the sliding element is displaceable in the direction of the sliding element longitudinal axis by rotating the distance-setting member about the distance-setting member rotational axis
   or
   b) the aligning apparatus comprises a base body on which the distance-setting member and the angle-setting member are rotatably mounted or held, and wherein the distance-changing device comprises a sliding element which is displaceably mounted on the base body and defines a sliding element longitudinal axis, which sliding element is arranged or formed cooperating directly or indirectly with the distance-setting member in such a way that the sliding element is displaceable in the direction of the sliding element longitudinal axis by rotating the distance-setting member about the distance-setting member rotational axis, and wherein the sliding element is guided on the base body so as to be non-rotatable in relation to the sliding element longitudinal axis.

4. Medical sawing template system in accordance with claim 3, wherein the base body comprises a sliding element guide in which the sliding element is moveably guided.

5. Medical sawing template system in accordance with claim 4, wherein at least one of
   a) the sliding element guide is configured in the form of a recess or perforation
   and
   b) the sliding element guide has a non-round cross section
   and
   c) the distance-changing device comprises a sliding catch arranged eccentrically to the distance-setting member rotational axis, wherein the sliding catch is arranged or formed on the distance-setting member and is moveably in engagement with the sliding element, or wherein the sliding catch is arranged or formed on the sliding element and is moveably in engagement with the distance-setting member
   or
   the distance-changing device comprises a sliding catch arranged eccentrically to the distance-setting member rotational axis, wherein the sliding catch is arranged or formed on the distance-setting member and is moveably in engagement with the sliding element, or wherein the sliding catch is arranged or formed on the sliding element and is moveably in engagement with the distance-setting member, and wherein the sliding catch is configured in the form of a pin, and wherein a pin longitudinal axis of the pin runs parallel or substantially parallel to the distance-setting member rotational axis
   or
   the distance-changing device comprises a sliding catch arranged eccentrically to the distance-setting member rotational axis, wherein the sliding catch is arranged or formed on the distance-setting member and is moveably in engagement with the sliding element, or wherein the sliding catch is arranged or formed on the sliding element and is moveably in engagement with the distance-setting member, and wherein the sliding catch engages into a corresponding guide recess for transmitting a drive force from the distance-setting member to the sliding element or the distance-changing device comprises a sliding catch arranged eccentrically to the distance-setting member rotational axis, wherein the sliding catch is arranged or formed on the distance-setting member and is moveably in engagement with the sliding element, or wherein the sliding catch is arranged or formed on the sliding element and is moveably in engagement with the distance-setting member, and wherein the sliding catch is configured in the form of a pin, and wherein a pin longitudinal axis of the pin runs parallel or substantially parallel to the distance-setting member rotational axis, and wherein the sliding catch engages into a corresponding guide recess for transmitting a drive force from the distance-setting member to the sliding element.

6. Medical sawing template system in accordance with claim 1, wherein the aligning apparatus comprises a base body on which the distance-setting member and the angle-setting member are rotatably mounted or held, and wherein the angle-changing device comprises a pivot element which is mounted on the base body so as to be pivotable about a pivot axis, which pivot element is arranged or formed cooperating directly or indirectly with the angle-setting member in such a way that the pivot element is pivotable about the pivot axis by rotating the angle-setting member about the angle-setting member rotational axis.

7. Medical sawing template system in accordance with claim 6, wherein at least one of a) the pivot axis runs parallel to the angle-setting member rotational axis and b) the first coupling member is arranged or formed, in particular in one piece, on the pivot element and c) the first coupling member defines a coupling member longitudinal axis, and wherein the coupling member longitudinal axis runs transversely to the sliding element longitudinal axis or the first coupling member defines a coupling member longitudinal axis, and wherein the coupling member longitudinal axis runs transversely to the sliding element longitudinal axis and the coupling member longitudinal axis runs transversely, in particular perpendicularly, to the pivot axis, and d) the base body comprises two bearing jaws, wherein the pivot element is mounted between the bearing jaws on a bearing pin held on the bearing jaws, or wherein the bearing jaws are mounted on two bearing projections projecting on the pivot element or the base body comprises two bearing jaws, wherein the pivot element is mounted between the bearing jaws on a bearing pin held on the bearing jaws, or wherein the bearing jaws are mounted on two bearing projections projecting on the pivot element, and wherein the bearing pin or the bearing projections define the pivot axis and e) the angle-changing device comprises a pivoting catch arranged eccentrically to the angle-setting member rotational axis, wherein the pivoting catch is arranged or formed on the angle-setting member and is moveably in engagement with the pivot element, or wherein the pivoting catch is arranged or formed on the pivot element and is moveably in engagement with the angle-setting member, or the angle-changing device comprises a pivoting catch arranged eccentrically to the angle-setting member rotational axis, wherein the pivoting catch is arranged or formed on the angle-setting member and is moveably in engagement with the pivot element, or wherein the pivoting catch is arranged or formed on the pivot element and is moveably in engagement with the angle-setting member, wherein at least one of b1) the pivoting catch is configured in the form of a pin, and wherein a pin longitudinal axis of the pin runs parallel or substantially parallel to the angle-setting member rotational axis and b2) the pivoting catch engages into a corresponding pivoting catch guide recess for transmitting a drive force from the angle-setting member to the pivoting element and b3) the pivot axis runs parallel or substantially parallel to the distance-setting member rotational axis.

8. Medical sawing template system in accordance with claim 1, wherein the angle-changing device comprises a pivoting catch arranged eccentrically to the angle-setting member rotational axis, wherein the pivoting catch is arranged or formed on the angle-setting member and is moveably in engagement with the pivot element, or wherein the pivoting catch is arranged or formed on the pivot element and is moveably in engagement with the angle-setting member, and wherein at least one of a) a distance of the pivot axis from the angle-setting member rotational axis is greater than a distance of the pivoting catch from the angle-setting member rotational axis and b) a distance of the sliding catch from the distance-setting member rotational axis is greater than a distance of the pivoting catch from the distance-setting member rotational axis and c) a distance of the pivot axis from the angle-setting member rotational axis is greater than a distance pivot axis from the pivoting catch.

9. Medical sawing template system in accordance with claim 1, wherein the distance-changing device is configured for varying the distance between the fastening element receptacle and the first coupling member in discrete distance steps.

10. Medical sawing template system in accordance with claim 9, wherein the discrete distance steps are the same size or substantially the same size.

11. Medical sawing template system in accordance with claim 1, wherein the distance-changing device comprises a distance step-setting device for setting discrete distances between the fastening element receptacle and the first coupling member.

12. Medical sawing template system in accordance with claim 11, wherein the distance step-setting device is configured in the form of a distance latching mechanism, comprising mutually cooperating first and second distance latching members, and wherein the first and second distance latching members are in engagement at discrete distances between the fastening element receptacle and the first coupling member.

13. Medical sawing template system in accordance with claim 12, wherein at least one of
   a) the first and second distance latching members are arranged or formed on the distance-setting member on the one hand and on the base body on the other hand
   and
   b) a plurality of first distance latching members is configured in the form of teeth forming a distance toothing
   or
      a plurality of first distance latching members is configured in the form of teeth forming a distance toothing, and wherein the distance toothing is arranged or formed concentrically surrounding the distance-setting member rotational axis
   and
   c) a second distance latching member is configured in the form of a distance latching body which is deflectable out of a base position against a biasing element
   or
      a second distance latching member is configured in the form of a distance latching body which is deflectable out of a base position against a biasing element, and wherein a direction of action of the biasing element runs parallel or substantially parallel to the distance-setting member rotational axis
   and
   d) the first distance latching members are arranged or formed projecting from the distance-setting member pointing in the direction toward the base body
   and
   e) a distance of the first distance latching members from the distance-setting member rotational axis is greater than a distance of the sliding catch from the distance-setting member rotational axis.

14. Medical sawing template system in accordance with claim 1, wherein the angle-changing device comprises an angle step-setting device for setting discrete angles between the fastening element receptacle and the first coupling member.

15. Medical sawing template system in accordance with claim 14, wherein the angle step-setting device is configured in the form of an angle latching mechanism comprising mutually cooperating first and second angle latching members, and wherein the first and second angle latching members are in engagement at discrete angles between the fastening element receptacle and the first coupling member.

16. Medical sawing template system in accordance with claim 15, wherein at least one of
   a) the first and second angle latching members are arranged or formed on the angle-setting member on the one hand and on the base body on the other hand
   and
   b) a plurality of first angle latching members is configured in the form of teeth forming an angle toothing
   or
      a plurality of first angle latching members is configured in the form of teeth forming an angle toothing, and the angle toothing is arranged or formed concentrically surrounding the angle-setting member rotational axis
   and
   c) a second angle latching member is configured in the form of an angle latching body which is deflectable out of a base position against a biasing element
   or
      a second angle latching member is configured in the form of an angle latching body which is deflectable out of a base position against a biasing element, and a common biasing element is associated with the second distance latching member and the second angle latching member
   and
   d) a second distance latching member is configured in the form of a distance latching body which is deflectable out of a base position against a biasing element, and a direction of action of the biasing element runs parallel or substantially parallel to the angle-setting member rotational axis
   and
   e) the first distance latching members are arranged or formed projecting from the angle-setting member pointing in the direction toward the base body
   and
   f) a distance of the first angle latching members from the angle-setting member rotational axis is greater than a distance of the pivoting catch from the angle-setting member rotational axis.

17. Medical sawing template system in accordance with claim 1, wherein at least one of
   a) the fastening element receptacle is arranged or formed on the sliding element, in particular in the form of a perforation which is rotationally symmetrical in cross section,
   and
   b) the medical sawing template system comprises at least one fastening element for anchoring in a bone
   or
      the medical sawing template system comprises at least one fastening element for anchoring in a bone, and the at least one fastening element is configured in the form of a bone pin or in the form of a bone screw.

18. Medical sawing template system in accordance with claim 1, further comprising a sawing template with at least one guide perforation, in particular in the form of a guide slot, for a saw blade.

19. Medical sawing template system in accordance with claim 18, wherein at least one of
   a) the sawing template comprises at least one sawing template fastening element receptacle for accommodating at least one fastening element
   and
   b) the sawing template comprises a second coupling member for bringing into engagement with the first coupling member
   and
   c) the sawing template is non-releasably connected to the first coupling member or is formed as one piece with the first coupling member
   and
   d) the sawing template comprises at least one first coupling element for bringing into engagement with a second coupling element of a medical referencing unit.

20. Medical sawing template system in accordance with claim 1, further comprising
   a) a medical referencing unit, the position and the orientation in space of which is determinable with a medical navigation system
   or
   b) a medical referencing unit, the position and the orientation in space of which is determinable with a medical navigation system, and the referencing unit is arranged or formed on the sawing template, or wherein the referencing unit comprises a second coupling element for bringing into engagement with the first coupling element of the sawing template in a coupling position.

\* \* \* \* \*